(12) United States Patent
Stanton et al.

(10) Patent No.: US 7,817,773 B2
(45) Date of Patent: Oct. 19, 2010

(54) VARIABLE SPEED THREE-DIMENSIONAL IMAGING SYSTEM

(75) Inventors: Martin Stanton, Concord, MA (US);
Alexander Stewart, Waltham, MA (US);
Gordon D Row, Groton, MA (US);
Timothy Lee Moulton, Boston, MA (US)

(73) Assignee: Dexela Limited, London (GB)

( * ) Notice: Subject to any disclaimer, the term of this patent is extended or adjusted under 35 U.S.C. 154(b) by 74 days.

(21) Appl. No.: 11/620,214

(22) Filed: Jan. 5, 2007

(65) Prior Publication Data

US 2008/0165916 A1    Jul. 10, 2008

(51) Int. Cl.
*H05G 1/60*     (2006.01)
*H05G 1/02*     (2006.01)

(52) U.S. Cl. .................................. 378/15; 378/193
(58) Field of Classification Search ............... 378/4–20, 378/37, 62, 126, 131, 193, 195–197, 210
See application file for complete search history.

(56) References Cited

U.S. PATENT DOCUMENTS

| | | | |
|---|---|---|---|
| 4,052,619 A | 10/1977 | Hounsfield | |
| 4,303,860 A | 12/1981 | Bjorkhom et al. | |
| 4,323,925 A | 4/1982 | Abell et al. | |
| 4,445,117 A | 4/1984 | Gaalema et al. | |
| 4,852,137 A | 7/1989 | Mackay | |
| 4,930,147 A * | 5/1990 | Dieterlen et al. | 378/176 |
| 4,942,597 A * | 7/1990 | Van Acker et al. | 378/197 |
| 4,970,398 A | 11/1990 | Scheid | |
| 4,998,270 A | 3/1991 | Scheid et al. | |
| 5,072,591 A | 12/1991 | Grange et al. | |
| 5,142,557 A | 8/1992 | Toker et al. | |
| 5,197,294 A | 3/1993 | Galvan et al. | |
| 5,216,250 A | 6/1993 | Pellegrino et al. | |
| 5,235,184 A | 8/1993 | Paulson | |
| 5,519,221 A | 5/1996 | Weinberg | |
| 5,533,087 A | 7/1996 | Snoeren | |

(Continued)

OTHER PUBLICATIONS

Hudson and Larkin (1994) "Accelerated Image Reconstruction Using Ordered Subsets of Projection Data" IEEE Transactions on Medical Imaging, 13(4):601-609.

(Continued)

*Primary Examiner*—Edward J Glick
*Assistant Examiner*—Anastasia Midkiff
(74) *Attorney, Agent, or Firm*—Swanson & Bratschun, L.L.C.

(57) ABSTRACT

A method and apparatus for imaging an object including the steps of projecting radiation from a radiation source through an object and moving the radiation source through multiple imaging positions relative to the object without stopping movement of the radiation source. Movement is accomplished while projecting radiation at more than one of the imagining positions with the source having a source velocity for at least one imaging position that is different from a source velocity for a second imaging position. Radiation transmitted through the object is also detected. Radiation may be projected while moving the radiation source through the multiple imaging positions. In addition, the velocity at which the radiation source is moved through a select imaging position may be related to a resolution desired for data collection at the select imaging position. The velocity of the radiation source may be varied within a select imaging position. Furthermore, the motion of the radiation source may be stopped at one or more of the imaging positions.

16 Claims, 11 Drawing Sheets

U.S. PATENT DOCUMENTS

| | | | |
|---|---|---|---|
| 5,550,380 A | 8/1996 | Sugawara et al. | |
| 5,550,386 A | 8/1996 | Kojima et al. | |
| 5,551,244 A | 9/1996 | Bailey | |
| 5,596,200 A | 1/1997 | Sharma et al. | |
| 5,604,781 A | 2/1997 | Suzuki et al. | |
| 5,617,461 A | 4/1997 | Schreiner | |
| 5,693,948 A | 12/1997 | Sayed et al. | |
| 5,852,646 A | 12/1998 | Klotz et al. | |
| 5,872,828 A | 2/1999 | Niklason et al. | |
| 5,891,959 A | 4/1999 | Kunz | |
| 5,896,437 A | 4/1999 | Ploetz | |
| 5,999,587 A | 12/1999 | Ning et al. | |
| 6,069,933 A | 5/2000 | Schultz | |
| 6,173,033 B1 | 1/2001 | Klingenbeck-Regn et al. | |
| 6,222,902 B1 | 4/2001 | Lin et al. | |
| 6,236,708 B1 | 5/2001 | Lin et al. | |
| 6,263,041 B1 | 7/2001 | Van Der Ende | |
| 6,265,736 B1 | 7/2001 | Dillen et al. | |
| 6,292,530 B1 | 9/2001 | Yavus et al. | |
| 6,373,917 B1 | 4/2002 | Roder | |
| 6,583,420 B1 | 6/2003 | Nelson et al. | |
| 6,611,575 B1 * | 8/2003 | Alyassin et al. | 378/37 |
| 6,618,468 B2 | 9/2003 | Klotz et al. | |
| 6,744,848 B2 | 6/2004 | Stanton | |
| 6,751,285 B2 | 6/2004 | Eberhard et al. | |
| 6,882,700 B2 | 4/2005 | Wang et al. | |
| 6,940,943 B2 | 9/2005 | Claus | |
| 6,999,553 B2 | 2/2006 | Livingston | |
| 7,319,735 B2 * | 1/2008 | Defreitas et al. | 378/37 |
| 7,412,026 B2 * | 8/2008 | Liu et al. | 378/62 |
| 2003/0095624 A1 * | 5/2003 | Eberhard et al. | 378/37 |
| 2003/0194050 A1 * | 10/2003 | Eberhard et al. | 378/37 |
| 2005/0105679 A1 | 5/2005 | Wu | |
| 2005/0129172 A1 * | 6/2005 | Mertelmeier | 378/37 |

OTHER PUBLICATIONS

Kamphuis and Beekman (1998) "Accelerated Iterative Transmission CT Reconstructions Using an Ordered Subsets Convex Algorithm" IEEE Transactions on Medical Imaging, 17(6):1101-1105.

Lange and Carson (1984) "EM Reconstruction Algorithms for Emission and Transmission Tomography" Journal of Computer Assisted Tomography, 8(2):306-316.

Lange and Fessler (1995) "Globally Convergent Algorithms for Maximum a Posteriori Transmission Tomography" IEEE Transactions on Image Processing, vol. 4, No. 10.

Lyon, et al. (1997) "A Maximum Entropy Method with a Priori Maximum Likelihood Constraints" The Astrophysical Journal, 478:658-662.

Manglos, et al. (1995) "Transmission Maximum-Likelihood Reconstruction with Ordered Subsets for Cone Beam CT" Physics Medicine and Biology, 40:1225-1241n.

Niklason, et al. (1998) "Digital Breast Tomosynthesis: Potentially a New Method for Breast Cancer Screening", Digital Mammography by Nijmegen, Kluwer Academic Publishers, pp. 51-56.

Shepp and Vardi (1982) "Maximum Likelihood Reconstruction for Emission Tomography" IEEE Transactions on Medical Imaging, Mi-1(2):113-121.

Skilling and Bryan (1984) "Maximum Entropy Image Reconstruction: General Algorithm" Monthly Notices of the Royal Astronomical Society, 211:111-124.

Wu (1997) "The Maximum Entropy Method" Springer Series in Information Sciences, VII:1-327.

International Search Report prepared by the U.S. Patent and Trademark Office as International Searching Authority, for PCT Application No. PCT/US2007/082137, Jun. 9, 2008, 4 pages.

* cited by examiner

VARIABLE SPEED THREE-DIMENSIONAL IMAGING SYSTEM

TECHNICAL FIELD

The present invention is directed to radiology imaging systems, and more particularly to a variable speed 3-dimensional imaging system.

BACKGROUND OF THE INVENTION

U.S. Pat. No. 6,744,848 (the "'848 patent"), the contents of which are expressly incorporated in its entirety herein, describes a method for creating low-dose three dimensional representations of an object. In summary, the '848 patent discloses that a three dimensional representation of an object can be created using a low radiation dose by creating a three dimensional representation with asymmetric resolution. For example, a useful three dimensional representation of an object can be created that has high resolution in two dimensions and only moderate resolution in the third dimension. If the lower resolution orientation is considered to be the "vertical" direction, then the reconstruction has a high-resolution horizontal plane.

The '848 patent discloses optimized data collection geometries that allow for the efficient acquisition of the data necessary to create the three dimensional representation. In brief, these geometries collect high-resolution data when imaging in a position normal to the high-resolution horizontal plane and lower-resolution data when imaging in a position normal to the lower-resolution vertical direction. The method disclosed in the '848 patent includes rotating a source and a detector about an axis of rotation around an object while maintaining radiation communication therebetween. Images are acquired at a variety of radial positions about the object to enable calculation of a three dimensional representation of the object from two dimensional images.

In practice, it has proven difficult to quickly move detectors and sources from one stationary position to another. In part this is due to the relatively high mass of the radiation source and detector. An inability to quickly move the detector between stations is particularly acute in applications where the total acquisition time must be minimized in order to avoid blurring caused by motion of the object or discomfort to a patient where a portion of the patient's anatomy serves as the object. Mechanical considerations such as residual vibrations have also proven difficult to eliminate when brining the source and detector to a complete stop when acquiring images at various positions.

The present invention is directed toward overcoming one or more of the problems discussed above.

SUMMARY OF THE INVENTION

A first aspect of the present invention is a method of imaging an object. The method includes the steps of projecting radiation from a radiation source through an object and moving the radiation source through multiple imaging positions relative to the object without stopping movement of the radiation source. Movement is accomplished while projecting radiation at more than one of the imagining positions with the source having a source velocity for at least one imaging position that is different from a source velocity for a second imaging position. Radiation transmitted through the object is also detected. Radiation may be projected while moving the radiation source through the multiple imaging positions. In addition, the velocity at which the radiation source is moved through a select imaging position may be related to a resolution desired for data collection at the select imaging position. The velocity of the radiation source may be varied within a select imaging position. Furthermore, the motion of the radiation source may be stopped at one or more of the imaging positions. For example, the source may be stopped at the highest desired resolution position which also allows a conventional two dimensional image to be obtained to supplement the three dimensional data.

Another aspect of the present invention is a method of imaging an object comprising moving a radiation source at a select velocity through multiple imaging positions relative to an object, projecting radiation at more than one select radiation dosage from the radiation source through the object and detecting the radiation transmitted through the object. The radiation dosage selected for at least one select imaging position may be related to a resolution desired for data collected at the select imaging position.

Yet another aspect of the present invention is a method of imaging an object comprising projecting radiation from a radiation source through an object while moving the radiation source through multiple imaging positions relative to the object. The velocity at which the radiation source is moved through a select imaging position may be related to a resolution desired for data collected at the select imaging position. This aspect of the invention also includes detecting the radiation transmitted through the object.

A further aspect of the present invention is an apparatus for imaging an object. The apparatus includes a radiation source for projecting radiation through an object. Means are provided for moving the radiation source through multiple imaging positions relative to the object wherein movement of the source is not stopped while projecting radiation at more than one of the imaging positions and the source velocity for at least one imaging position is different from a source velocity for a second imaging position. Detection means are included to detect the radiation transmitted through the object.

Another aspect of the present invention is an imaging apparatus providing a radiation source and a radiation detector. The radiation source and the radiation detector are coupled for rotation in an X-Z plane about a common axis of rotation while maintaining radiation communication therebetween. A platform is configured to maintain an object in a fixed position relative to and between the radiation source and the radiation detector. The radiation source, the radiation detector and the platform are operatively associated for vertical movement along a Z-axis without movement relatively to one another along the Z-axis. In one embodiment the platform is configured for rotation about the common axis of rotation. In either embodiment the imaging system may further include a paddle operatively associated with the platform, the paddle being moveable substantially normal to a surface of the platform to selectively secure and release an object between the surface of the platform and the paddle. In such an embodiment, a clutch may be operatively associated with the paddle to prevent more than the select force from being applied to an object between the surface of the platform and the paddle. In another embodiment the imaging apparatus further includes a rotor arm rotatable about the common axis of rotation, the radiation source and the radiation detector being attached to the rotor arm on opposite sides of the axis of rotation. Such an embodiment may further include a shaft extending along the axis of rotation, the rotor arm being operatively associated with the shaft for rotation about the shaft and the platform being operatively associated with the shaft for select rotation about the shaft independent of rotation of the rotor arm about the shaft. This embodiment may further include the shaft being fixedly mounted to a carriage and a carriage being attached through a support extended along a Z-axis for select movement relative to the support along the Z-axis to provide the operative association for vertical movement of the radiation source, the radiation detector and the platform. Such an embodiment may further include an actuator operatively associated with the carriage for further providing select movement along the Z-axis.

Another aspect of the present invention is an imaging apparatus comprising a radiation source and a radiation detector. The radiation source and the radiation detector are coupled for rotation in an X-Z plane about a common axis of rotation while maintaining radiation communication therebetween. A platform is configured to maintain an object in a fixed position relative to and between the radiation source and the radiation detector. The platform is configured for rotation about the common axis of rotation. In one embodiment, a paddle is operatively associated with the platform, the paddle is moveable substantially normal to the surface of the platform to selectively secure and release an object between the surface of the platform and the paddle. Such an embodiment may further include a clutch operatively associated with the paddle to prevent more than a select force from being applied to an object between the surface of the platform and the paddle. In another embodiment, the radiation source, the radiation detector and the platform are operatively associated for vertical movement along a Z-axis without movement relative to one another along the Z-axis.

Yet another embodiment includes a rotor arm rotatable about the axis of rotation, the radiation source and the radiation detector being attached to the rotor arm on opposite sides of the axis of rotation. Such an embodiment may further include the shaft extending along the axis of rotation, the rotor arm being operatively associated with the shaft for rotation about the shaft and the platform being operatively associated with the shaft for select rotation about the shaft independent of rotation of the rotor arm about the shaft. Such an embodiment may further include the shaft being fixedly mounted to a carriage and the carriage being attached to a support extending along the Z-axis for select movement relative to the support along the Z-axis. An actuator may be operatively associated with the carriage for providing select movement along the Z-axis.

Yet another aspect of the invention is an imaging apparatus comprising a radiation source and a radiation detector having a detecting surface. The radiation source and the radiation detector are coupled for rotation in an X-Z plane about a common access of rotation while maintaining radiation communication therebetween. The radiation detector is further configured for movement between a first position relatively near the radiation source and a second position relatively far from the radiation source. One embodiment further includes control means for controlling the radiation source and the radiation detector to collect standard 2-dimensional images with the detector in the first position and tomosynthesis images with the detector in the second position. In such an embodiment the control means may further prevent rotation of the radiation source as the radiation detector with the radiation detector in the first position. Another embodiment includes a removable platform configured in operative engagement with the radiation source and the radiation detector to maintain an object in a fixed position between the radiation source and the radiation detector. The radiation source, radiation detector and the removable platform are configured so that with the radiation source and the radiation detector aligned along the Z-axis and the platform removed, the radiation detector is moveable into the first position. Such an embodiment may further include the radiation source, the radiation detector and the removable platform being configured so that the radiation detector is moveable into the second position only with the platform in operative engagement with the radiation source and the radiation detector.

In another embodiment the imaging apparatus further includes a platform configured in operative engagement with the radiation source and the radiation detector to maintain an object in a fixed position between the radiation source and the radiation detector, the platform having a thickness thin enough to allow the detector to reach the first position.

Those embodiments including the control means may further include a control means providing rotation of the radiation source and the radiation detector at a first rate with the detector in the first position and a second rate with the detector in the second position, the first rate being less than the second rate. Those embodiments including the control means may further include a counterweight operatively associated with the detector to move in a direction opposite the detector as the detector moves between the first and second positions to maintain balance between the radiation source and the radiation detector.

Another embodiment of this aspect of the invention may comprise a rotor arm rotatable about the common axis of rotation, the radiation source and the radiation detector being attached to the rotor arm on opposite sides of the axis of rotation. Such an embodiment may further include a removable platform configured in operative engagement with the radiation source and the radiation detector to maintain an object in a fixed position relative to the axis of rotation between the radiation source and the radiation detector. A shaft may extend along the axis of rotation, the rotor arm being operatively associated with the shaft for rotation about the shaft and the platform being operatively associated with the shaft for select rotation about the shaft independent of rotation of the rotor arm about the shaft. Such an embodiment may further include a rail on the rotor arm on a side of the rotor arm carrying the radiation detector. The radiation detector is attached to the rail for movement along the rail between the first and second positions. A motorized screw may be provided in operative association with the radiation detector to move the radiation detector between the first and second positions. An encoder may be operatively associated with the motorized screw drive.

Yet another aspect of the present invention is an imaging apparatus comprising a radiation source and a radiation detector. Rotating means are provided for rotating the radiation source and the radiation detector in an X-Z plane about a common axis of rotation while maintaining radiation communication therebetween. Means are provided for securing an object between the radiation source and the radiation detector. Means are further provided for accelerating and decelerating the radiation source and detector between detectable imaging positions. Damping means are further provided for damping vibration of the radiation source, the radiation detector and the securing means relative to one another during rotation of the radiation source and the radiation detector. In one embodiment the rotating means comprises a rotor arm rotatable about the axis of rotation, the radiation source and the radiation detector being attached to the rotor arm on opposite sides of the axis of rotation. In such an embodiment the damping means comprises a shaft extending along the axis of rotation, the rotor arm being operatively associated with the shaft for rotation about the shaft, the platform being operatively associated with the shaft. In such an embodiment, the platform may be operatively associated with the shaft for select rotation about the shaft independent of rotation of the rotor arm about the shaft. The shaft may be fixedly mounted to a carriage and the carriage may be attached to a support extending along the Z-axis for select movement relative to the support along the Z-axis. In any embodiment, the damping means may provide a sufficiently high electronic frequency to substantially settle the radiation source, the radiation detector and the platform relative to one another within about 0.067 seconds.

DETAILED DESCRIPTION OF THE INVENTION

As described above, known methods and systems for acquiring the multiple sub-images necessary to create a three-dimensional image of an object or scene are limited because it is difficult to quickly move a radiation source, detector or source-detector pair from one stationary position to another. In particular, mechanical considerations make it difficult to bring the moving, typically rotating, imaging apparatus to a complete stop when acquiring an image at each imaging position without the introduction of image blurring vibrations. Also, in many biological or medical applications such as the 3-D imaging of a breast or other body part, stopping the imaging apparatus at each imaging position can substantially increase total acquisition time. Generally, it is desirable to minimize total acquisition time to avoid the potential for patient movement induced blurring.

The imaging system methods and apparatus described herein include embodiments where the operative components of an imaging apparatus, for example, the radiation source or detector array, do not have to be made stationary when each individual sub-images is collected. On the contrary, embodiments described include methods and apparatus where the operative components of an imaging system may continue to move at a suitable velocity during the acquisition of some or all sub-images with the velocity chosen to facilitate a desired resolution or an image or to avoid unacceptable degradation of the desired 3-D representation of the subject object.

Figure 1:
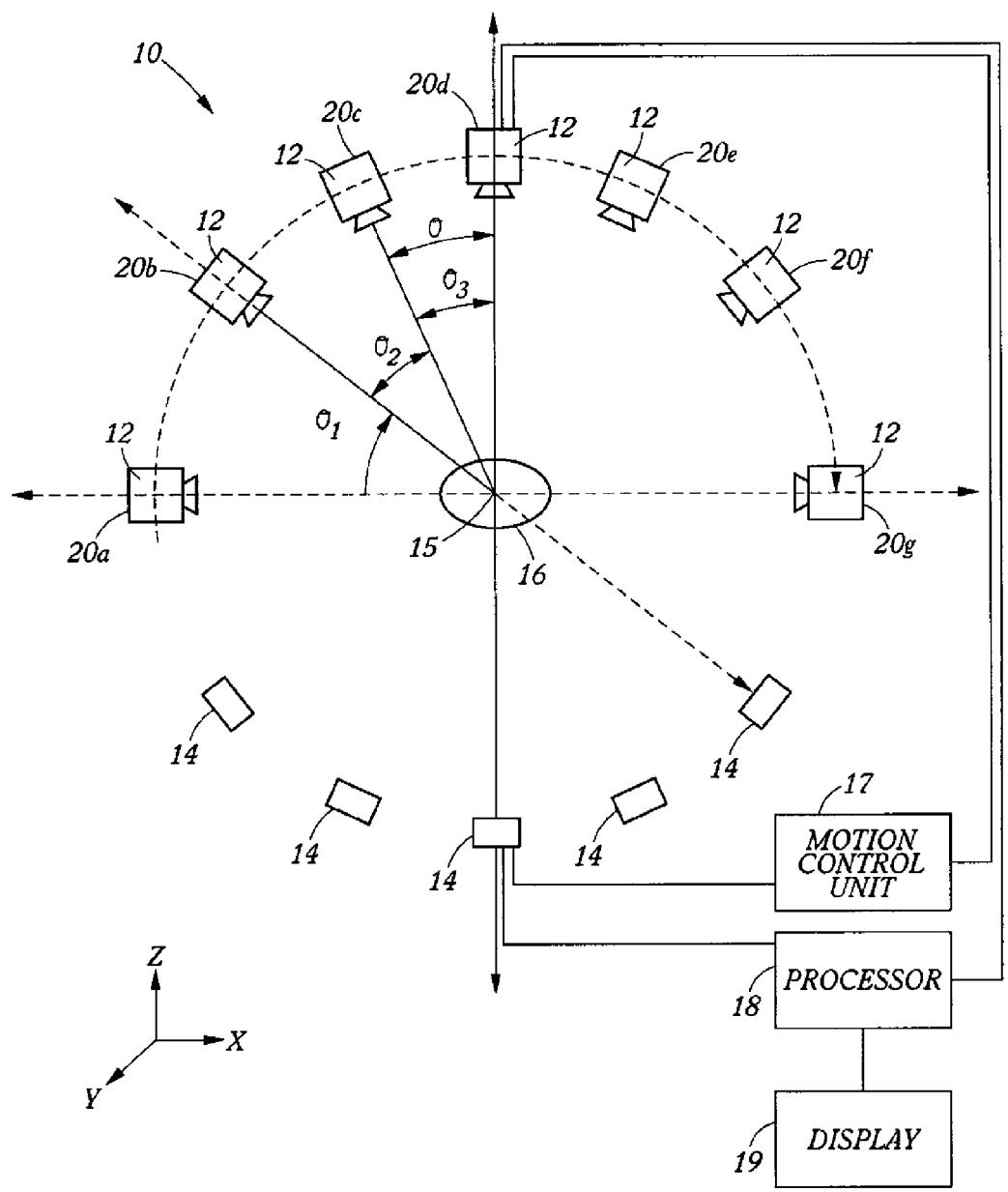
FIG. 1 is a schematic representation of an embodiment of an imaging apparatus.

For the purposes of illustration and discussion below, it is assumed that the imaging apparatus 10 is configured as schematically represented in FIG. 1. In this embodiment, the source 12 and detector 14 are moved together around a pivot point or axis of rotation 15 centered on the object being imaged. The source 12 and the detector 14 are moved by the motion control unit 17 in a manner discussed in greater detail below. Processor 18 is coupled to the motion control unit 17, source 12, detector 14 and display 19. The processor 18 dictates any movement of the source 12 and detector 14 and further is programmed to control image capture and image processing. Display 19 displays the captured or processed images. The processor can comprise any manner of digital processor such as a microprocessor, personal computer or workstation and associated controlling software. The object being imaged is shown on FIG. 1 as a breast 16. The object could be any desired object, such as other portions of human and animal bodies, other organic or inorganic objects or containers such as luggage. However, the imaging apparatus 10 as described herein is particularly well suited for imaging anatomical objects such as the breast 16.

FIG. 1 further illustrates a possible strategy for moving or rotating the source 12 and detector 14 pairs to multiple imaging positions 20a, 20b, 20c . . . 20n with respect to the object. Each imaging position 20a, 20b, 20c . . . 20n may be separated from other imaging positions by a select angular spacing $\Theta_1$, $\Theta_2$, $\Theta_3$ . . . $\Theta_n$ as illustrated on FIG. 1. As described in detail below, the angular spacing $\theta$ between imaging positions 20 may be uniform or non-uniform.

The apparatus 10 illustrated in FIG. 1 is only one potential configuration for an imaging apparatus suitable for the implementation for the methods disclosed herein. Alternative embodiments of an imaging apparatus 10 might feature either a stationary source 12 or stationary detector 14. Alternatively both the source 12 and detector 14 might be held stationary with respect to the object with separate radiation projection or radiation detection apparatus being moved with respect to the object. Movement may be caused by optical, optical/mechanical, or optical electrical linkages including lenses, mirrors, fiber optics, prisms, wave guides or other components known in the art. Thus, the phrase, "moving a radiation source" or "moving the detector" as used herein, is defined broadly to include actually moving the source 12 and detector 14 or moving a projection or detection apparatus associated with the source 12 or detector 14.

Similarly, the methods and apparatus described herein may be implemented with imaging geometries other than that schematically illustrated in FIG. 1. The FIG. 1 embodiment features a source 12 and detector 14 which rotate around a pivot point 15 causing radiation projected at each imaging position 20a, 20b, 20c . . . 20n to travel along a linear ray which passes substantially through the pivot point 15. Other embodiments may feature geometries which vary from the circular geometry illustrated in FIG. 1. In particular, if a select one of the source 12 and detector 14 is the only moving component, a half-circular geometry may be utilized. This and other geometries will have certain advantages for the imaging of specific objects.

In certain embodiments disclosed herein, the radiation source 12 moves through some or all the multiple image positions without coming to a full stop during the imaging process. As described above, the phrase "a moving radiation source" is defined broadly to indicate that the ray along which radiation is projected through an object is moving at one or more select velocities, or at a varying velocity. The movement of this projection ray may be accomplished with or without physically moving the source as described above. The velocity of the radiation source for a select one imaging position 20a may be different than the velocity of the radiation source at a second imaging position, for example, 20b. The velocity of the radiation source 12 may be changing through an imaging position 20 or may become zero (stationary) at a select imaging position. In certain embodiments it may be desirable to obtain a stationary highest resolution image at the appropriate position which highest resolution image can serve as a two dimensional compliment (a conventional mammogram for example) to the three dimensional data. The radiation source may be accelerated, decelerated, or both accelerated and decelerated between imaging positions 20. The dosage of radiation projected from the imaging source may be the same for each imaging position 20 or different among select imaging positions 20. In summary, one aspect of the present invention provides for the variation of select imaging parameters which include but are not limited to the following:

a. Uniformly spaced imaging positions 20;
b. Non-uniformly spaced imaging positions 20;
c. Uniform radiation dosage for each imaging position;
d. Non-uniform radiation dosage for each imaging position;
e. Both acceleration and deceleration between imaging positions; and
f. Only acceleration, deceleration or constant velocity between image positions 20.
g. Variable velocity through an imaging position 20.
h. Stopping movement at one or more select imaging positions 20.

Furthermore, for the purposes of illustrating the apparatus disclosed herein, it is assumed that it is desirable to have high image resolution in horizontal planes through the object with only moderate or relatively lower image resolution required in vertical planes through the object. The distinction of high resolution horizontal planes and relatively low resolution vertical planes is arbitrary and used for discussion purposes only in the examples set forth below. Embodiments may be implemented with any combination of variable resolutions desired. Thus, it will be assumed that a useful three-dimensional representation of an object can be created that has high resolution in two dimensions (assumed to be horizontal) and relatively lower resolution in the third dimension (assumed to be vertical). For example, in breast cancer screening, these dimensions might be 0.05 millimeter×0.05 millimeter×1 millimeter along the x, y and z axes, respectively. As noted above, the present invention includes a radiation source which may be moved through an imaging position during sub-image acquisition with or without coming to a full stop. It is important, however, that the motion of the detector and/or the source not introduce a blurring of the acquired image sub-component which would ultimately degrade the 3-D representation of the object beyond the desired asymmetric resolution of the desired representation. In the examples described below, more movement-induced blurring is acceptable in the vertical (low-resolution) orientation than in the horizontal (high-resolution) orientation.

Figure 2A:
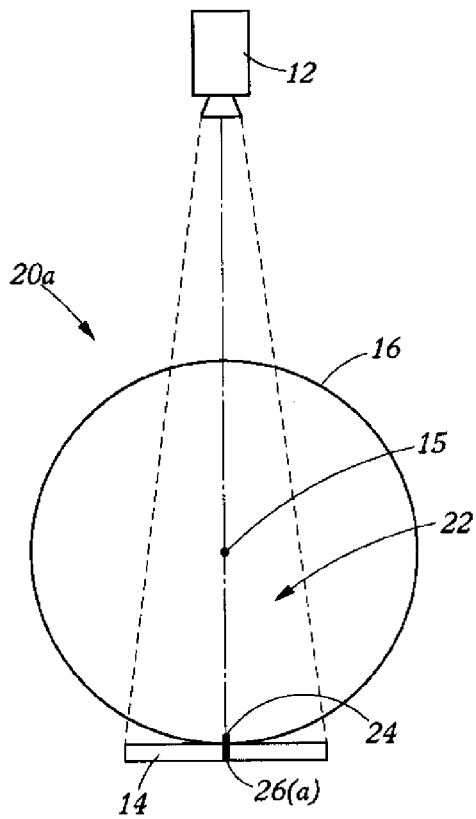
FIGS. 2A and 2B are schematic representations of the apparatus of FIG. 1 acquiring an image at two imaging positions.

FIG. 2A is a schematic illustration of an apparatus and method which is acquiring a single image in the series of sub-images where the detector 14 and source 12 are moving relative to the object. As illustrated in FIG. 2A, source 12 and detector 14 are rotated with a given angular velocity around a pivot 15 or axis of rotation to acquire or collect one of a series of images for time (t) through a section of the object defined herein as the image area 22. For this select sub-image, the source 12 and detector 14 move from image position 20a to 20b (see FIG. 2B) during image acquisition time (t). During (t), the projection of a point 24 in the object on to the detector 14 will move from a first projection point 26(a) (FIG. 2A) across the detector to a new projection point 26(b) (FIG. 2B).

In this illustration, the projection of the indicated point would move across the detector through the shaded area 28. The projection of this movement back into the object must be less than the required image resolution if motion induced blurring is to be maintained below the desired resolution. For example, if the desired resolution in the horizontal orientation is 0.05 mm, then the movement of the projection of the point across the detector from 26(a) to 26(b) should not exceed 0.05 mm.

Figure 2B:
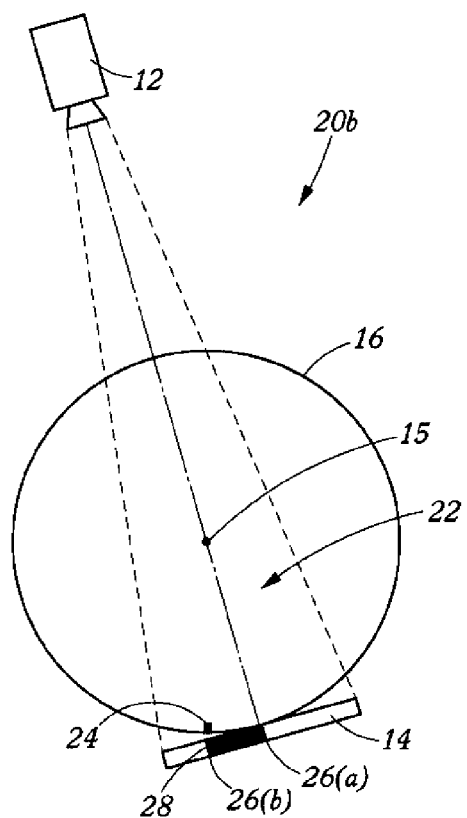
Figure 3A:
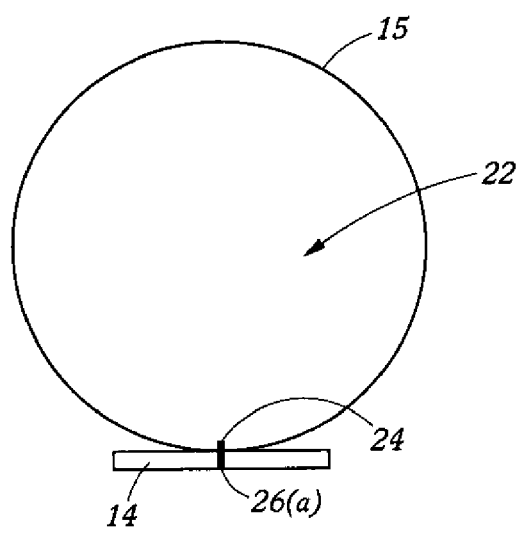
FIGS. 3A and 3B are a schematic representation illustrating a substantially "linear" movement of the detector between two positions.
Figure 3B:
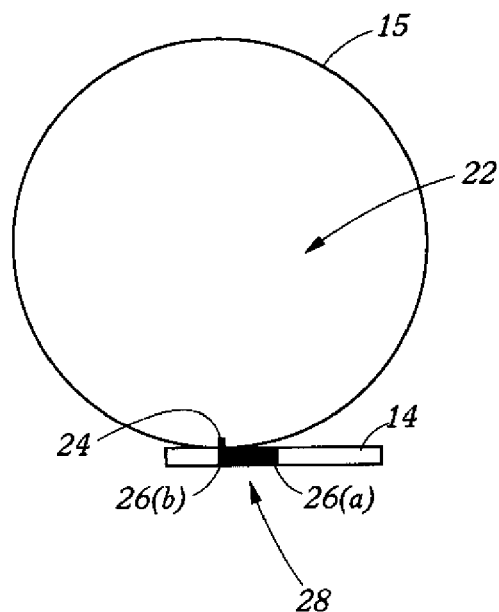

For purposes of further illustration, the example of FIGS. 2A and 2B can be simplified by assuming that the desired resolution is small relative to the imaging area 22 and that the distance between the imaging area 22 and the source 12 is large relative to the imaging area 22. Accordingly, as illustrated in FIGS. 3A and 3B, the detector 14 can be thought of as moving linearly relative to the image area 22 from position 26(a) to position 26(b). Therefore, the projection of the point in the object 24 onto the detector moves linearly from position 26(a) to 26(b). As above, when projected back into the image area 22, the region between 26(a) and 26(b) (illustrated as shaded area 28) must be less than the required resolution. In this example then, in recognition of the linear movement assumption, the velocity of the moving detector 14 multiplied by the image acquisition time (t) must be less than or equal 0.05 mm.

For purposes of illustration, the geometry described immediately above shall be used in the examples provided below, however, it should be recognized that other geometries can be derived from the concepts illustrated on FIGS. 2A, 2B, 3A and 3B. For example, angular positions and angular velocities can be inter-converted by the distance between the detector and the axis of rotation. It also should be recognized that in the above discussion, the point 24 in the area 22 was placed adjacent to the detector 14 such that there was a 1:1 projection from the detector back into the image area. Other geometries may have a different projection ratio. The geometrical relationships described above can be leveraged to achieve specific imaging goals. For example, the source velocity can be greater where less resolution is necessary and lesser where greater resolution is desired.

Figure 4:
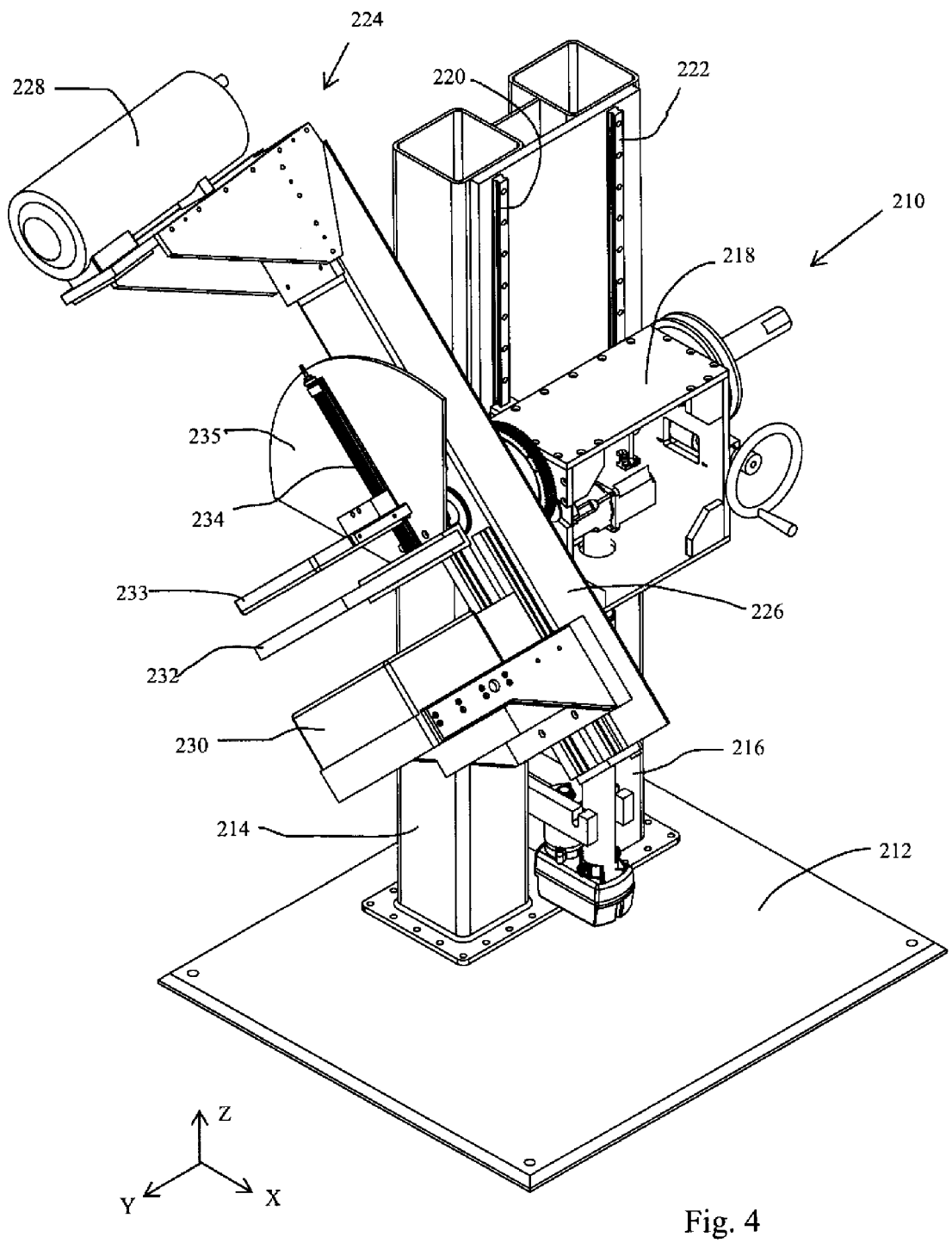
FIG. 4 is a perspective view of an imaging apparatus.

A representative embodiment of an imaging apparatus 210 is depicted in a perspective view in FIG. 4. The imaging apparatus 210 includes a base 212 and a pair of vertical supports 214, 216 extending normally from the base 212. A carriage 218 rides on a pair of rails 220, 222 attached to the vertical supports 214, 216 to enable vertical movement of the carriage 218 along a Z-axis in the vertical direction. A gantry 224 is rotatably attached to the carriage 218. The gantry 224 includes a rotor arm 226. A radiation source 228 is attached to a first end of the rotor arm 226 and a radiation detector 230 is attached to a second end of the rotor arm opposite the first end and on opposite ends of the pivot point or axis of rotation 15 along a Y-axis. In FIG. 4 the gantry as illustrated is rotated in an X-Z plane about the Y-axis at an angle of about 40° from vertical. A platform 232 is operatively associated with the carriage 218 to rotate about the axis of rotation independent of the rotation of the rotor arm 226. A paddle 233 is moveable in a direction normal to a surface of the platform 232 along a rail 234 to allow for securing an object to the platform 232 between the radiation source 228 and the radiation detector 230. The rail 234 is attached to a shield 235. The shield 235 is, like the platform 232, operatively associated with the carriage 218 to rotate about the axis of rotation with the platform 232. The shield 235 may include further shielding elements above and below the axis of rotation to protect a patient from the rotating gantry, but these shielding elements are not illustrated for the sake of clarity. The reference numbers used with respect to FIG. 4 will be used with like elements in other figures discussed herein.

Figure 5:
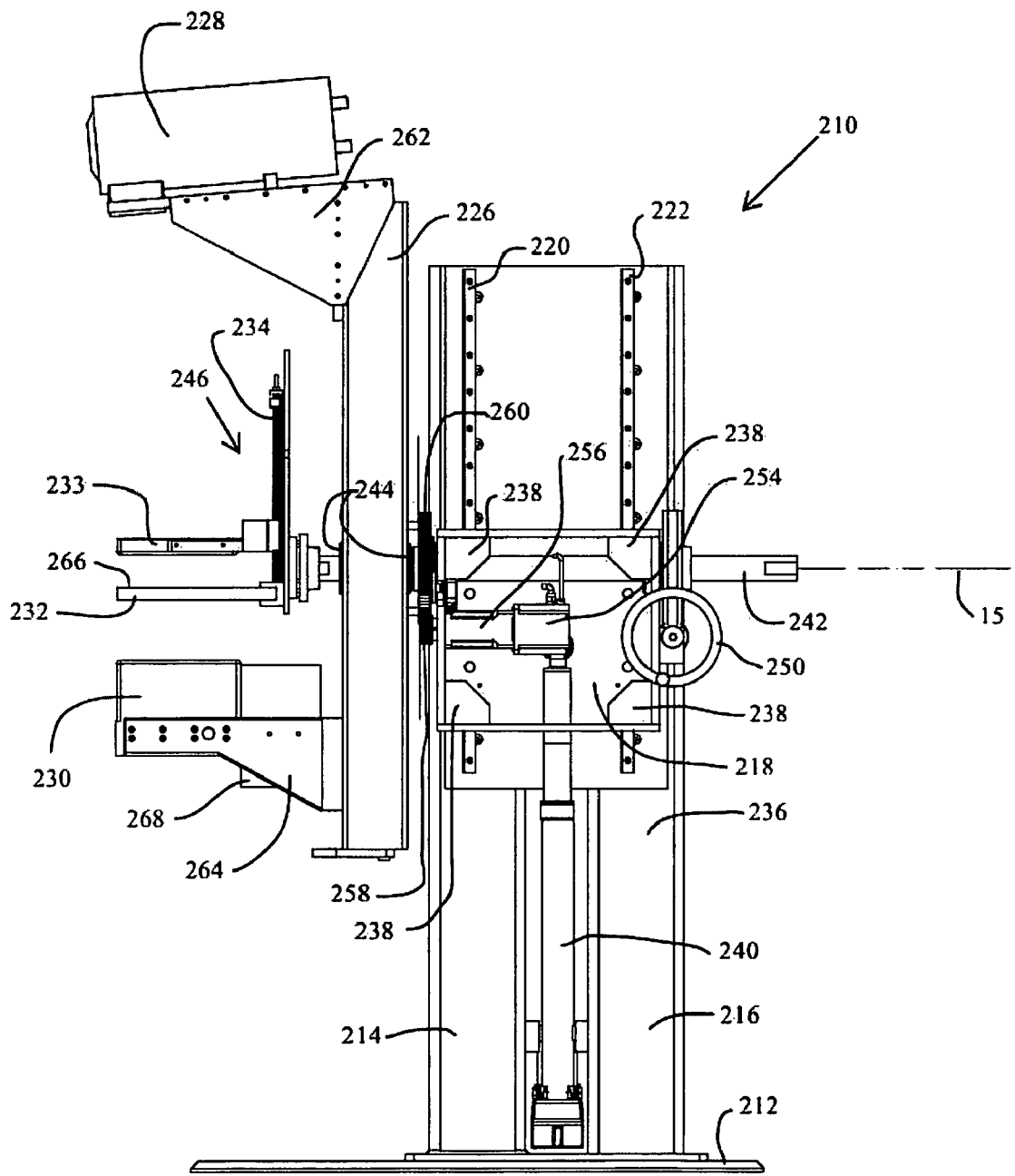
FIG. 5 is a right side elevation view of the imaging apparatus of FIG. 4.
Figure 6:
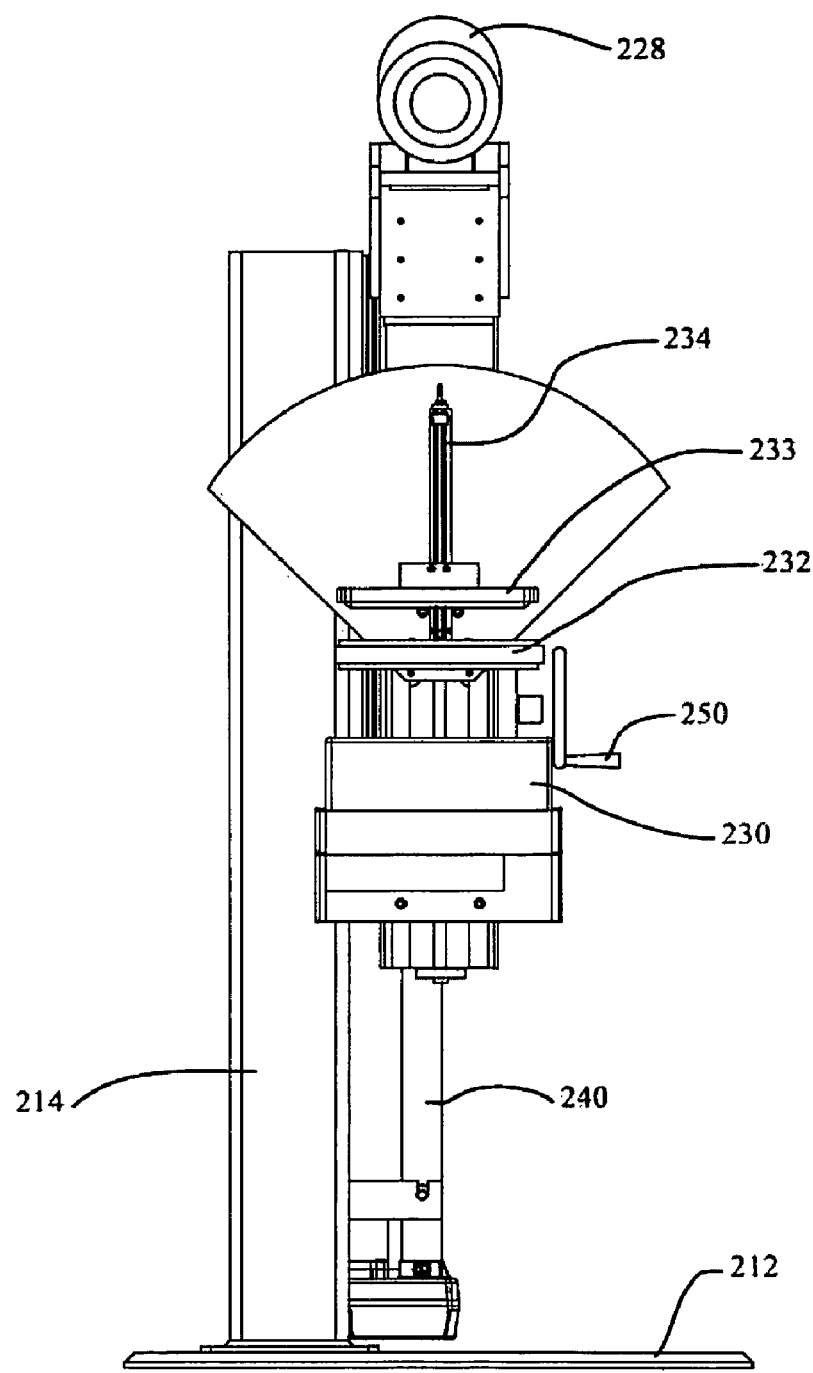
FIG. 6 is a front elevation view of the imaging apparatus of FIG. 5.

FIG. 5 is a side view of the imagining apparatus 210 of FIG. 1. The base 212 and vertical supports 214, 216 in the embodiment described herein are made of heavy gauge steel to provide rigidity and to minimize vibration. The base plate must be sufficiently heavy and rigid to enable the imaging apparatus to be free standing and stable. For example, a 32×36 inch footprint has provided adequate stability. The vertical supports may be made of, in one example, 6×6 inch structural steel tubing and are affixed to the base 212 by any suitable means including welding and bolting. A steel plate 236 spans a distal portion of the vertical supports 214, 216 and is rigidly secured thereto by any suitable means. The rails 220, 222 are likewise rigidly secured to the steel plate 236.

The carriage 218 is a five sided box made of steel plates which are fixedly attached by, for example, welding or rigid fixtures. Corner gusset plates 238 may be used to provide further rigidity and minimize flexure to the carriage 218. The back of the carriage box is attached to the rails 220, 222 by suitable runners with high tolerance wheels that provide minimal play between the carriage and the rails during rotation of the gantry 224. For example, preloaded bearings may be employed. The carriage 218 is raised and lowered along the Z-axis relative to the vertical supports 214, 216 by an actuator 240 which an operator may control by foot peddles or other suitable controls (not shown). The actuator 240 in the present embodiment is a vertical moving linear rotor with a single point of attachment to the carriage 218.

A rigid shaft or axle 242 extends along the axis of rotation 15 through and is attached to the carriage by preloaded bearings (not shown). In the present embodiment, the shaft 242 is 40 mm solid steel. A thick-walled hollow shaft may also be suitable and may also provide a conduit for various control cables. The rotor arm 226 is attached for rotation about the shaft by preloaded bearings 244.

An object immobilizer 246 consists of the platform 232 and the paddle 233. While any number of objects such as various portions of the human body may be imaged using the imaging apparatus 210, the embodiment described herein is particularly well suited for mammography. Thus the object immobilizer 246 would then function as a breast immobilizer. The breast immobilizer 246 is affixed to the rigid shaft 242 in a manner allowing rotation of the breast immobilizer 246 about the axis of rotation 15 along the shaft 242 independent of rotor arm 226 rotation. In the embodiment illustrated in FIG. 5, the platform 232 lies slightly below the axis of rotation 15, for example about 3 cm. The paddle 233 can be raised and lowered on the rail 234 between about 2-15 cm above a top surface of a platform 232. The paddle 233 is raised and lowered by actuation of a suitable mechanical linkage to the paddle. A clutch mechanism may be provided in the mechanical linkage to insure that the compression force on an object, such as a breast, does not exceed 40 pounds. In embodiment, the platform 242 is made of a radiation transmissive material such as carbon fiber. The paddle 233 may be a conventional mammography paddle or made of any radiation transmissive material suitable for securing the object under examination.

As discussed above, the breast immobilizer 246 is rotatable about the axis of rotation or the axis of the shaft 242 independent of rotation of the rotor arm 226. In the illustrated embodiment, the breast immobilizer 246 and the shield 235 are fixedly attached to the shaft 242 for rotation with the shaft 242. A hand crank 250 is mechanically linked to the shaft 242, by for example a worm gear (not shown) to enable rotation of the shaft 242 and thus the breast immobilizer and shield about the axis of rotation. A motor may be substituted for the hand crank 250. This enables collection of images from a number of vantage points. For example, where the object is a breast the vantage points can include cranio caudal (CC) and mediolateral oblique (MLO) views.

The rotor arm 226 is driven by a motion control unit 17 including a DC-servo motor 254 rigidly secured to the carriage 218. The drive shaft of the DC-servo motor 254 is linked to a two-stage planetary gear 256 which, in the present embodiment, has a 40 to 1 reduction. The two-stage planetary gear 256 is operatively associated with a pair of spur gears 258, 260 which collectively provide another 4 to 1 reduction. The spur gear 260 is fixedly attached to the rotor arm 226 to directly drive the rotor arm 226. All of the gears are very tightly meshed for high precision movement with minimal play. This combination of gears provides a total reduction of approximately 160 to 1. In this manner the DC-servo motor 254 which operates at speed of up to about 3000 RPM, can rotate the rotor arm 226 at up to about 20 RPM while providing ample torque. This mechanism further provides for precise computer-control angular positioning (accuracy better than 0.1°) as well as high rotation speed movements. In the present embodiment, the gantry can be rotated from −160° to +160° from vertical, allowing tomosynthesis MLO or CC data to be acquired on either breast. Rotation can be limited to this range by, for example, limit switches.

The radiation source 228 and the radiation detector 230 are attached to opposite ends of the rotor arm 226 by steel mounting brackets 262, 264, respectively. In the embodiment described herein, the radiation source 228 may be an x-ray tube such as a Varian RU70 that is positioned such that the focal spot of the tube is about 65 cm from the axis of rotation and is aligned on a line normal to a front surface 266 of platform 232. In this embodiment the x-ray tube may be powered by a Sedecal SHF1030M that allows multiple exposures to be taken in rapid succession at varying energies and doses.

Further describing the present embodiment, the detector 230 may be an x-ray detector which may either be a custom charged couple device (CCD-based x-ray detector) or a commercial detector such as the Anrad LMAM detector. A suitable CCD detector provides very low noise, high resolution and a readout in less than two seconds when used in a binned-mode. A readout in less than one second provides further advantages. A surface of the detector 230 in the present embodiment is mounted about 15 cm from the axis of rotation.

In use, the gantry 224 is capable of rotation about the shaft 242 at speeds up to 20 RPM. To minimize stress on the mechanics of the system and to minimize vibrations, the detector and source should be balanced about the axis of rotation 15. In the present embodiment the source weighs approximately 45 pounds and the detector weighs approximately 80 pounds with significantly different moment arms relative to the common axis of rotation 15 the shaft 242. Accordingly, weights 268 are added to the detector mounting bracket 264 to balance the gantry.

Use of the imaging apparatus 210 will be discussed in a mammography application. A patient will be fit to the imaging apparatus by facing the apparatus and a technician raising or lowering the breast immobilizer 246 by actuation of the actuator 240 and appropriate resulting the movement of the carriage 218. The side mount of carriage 218 to the vertical supports 214, 216 allows easy technician access to the patient's breast and the apparatus while maximizing patient comfort. It will be appreciated that because the gantry 224 and the breast immobilizer 246 are both attached to the shaft 242, they will move vertically in concert with the carriage 218. The breast is then placed on the platform 232 and compressed and secured in place by lowering the paddle 235 by means of the crank 250. Because the breast immobilizer 246 may be rotated about the axis of rotation, an operator can capture images from a variety of views such as CC and MLO on either patient breast.

During image capture the radiation source 228 and detector 230 are rotated about the axis of rotation while maintaining radiation communication therebetween. The breast immobilizer 246 including the platform 232 maintains the breast in a fixed position relative to and between the radiation source and the radiation detector. The DC-servo motor 254 and the associated two-stage planetary gear 256 and spur gears 258, 260 allow for rapid acceleration and deceleration of the radiation source 228 and the radiation detector 230 between multiple imagining positions.

The resulting vibrations caused by movement of the gantry between the multiple imaging positions is damped by a number of means, including a number of structural elements. These structural elements include balancing of the source and detector about the axis of rotation of the rotor arm 226, high precision, preloaded bearings 244 attaching the rotor arm to the shaft 242, the tight fit between the spur gears and the planetary gear, the high tolerance fit utilizing preloaded bearings between the runner of the carriage and the rails 220, 222 and the rigid vertical supports 214, 216 and base 212.

The present embodiment is designed to provide a relatively high harmonic frequency to promote rapid dissipation of vibration. The present embodiment has a harmonic frequency of about 30 Hz which means the apparatus is substantially settled in about 0.067 seconds. The term "substantially settled" means the vibrations have been sufficiently dampened to allow capture of an image with the necessary resolution.

A further means for minimizing the effect of any residual vibration is provided by the object immobilizer 246, radiation source 228 and radiation detector 230 having common attachment to the shaft 242. This minimizes the effect any residual vibrations in the system during image capture by providing the same relative movement between the radiation source 228, the radiation detector 230 and the object immobilizer 246.

Figure 7:
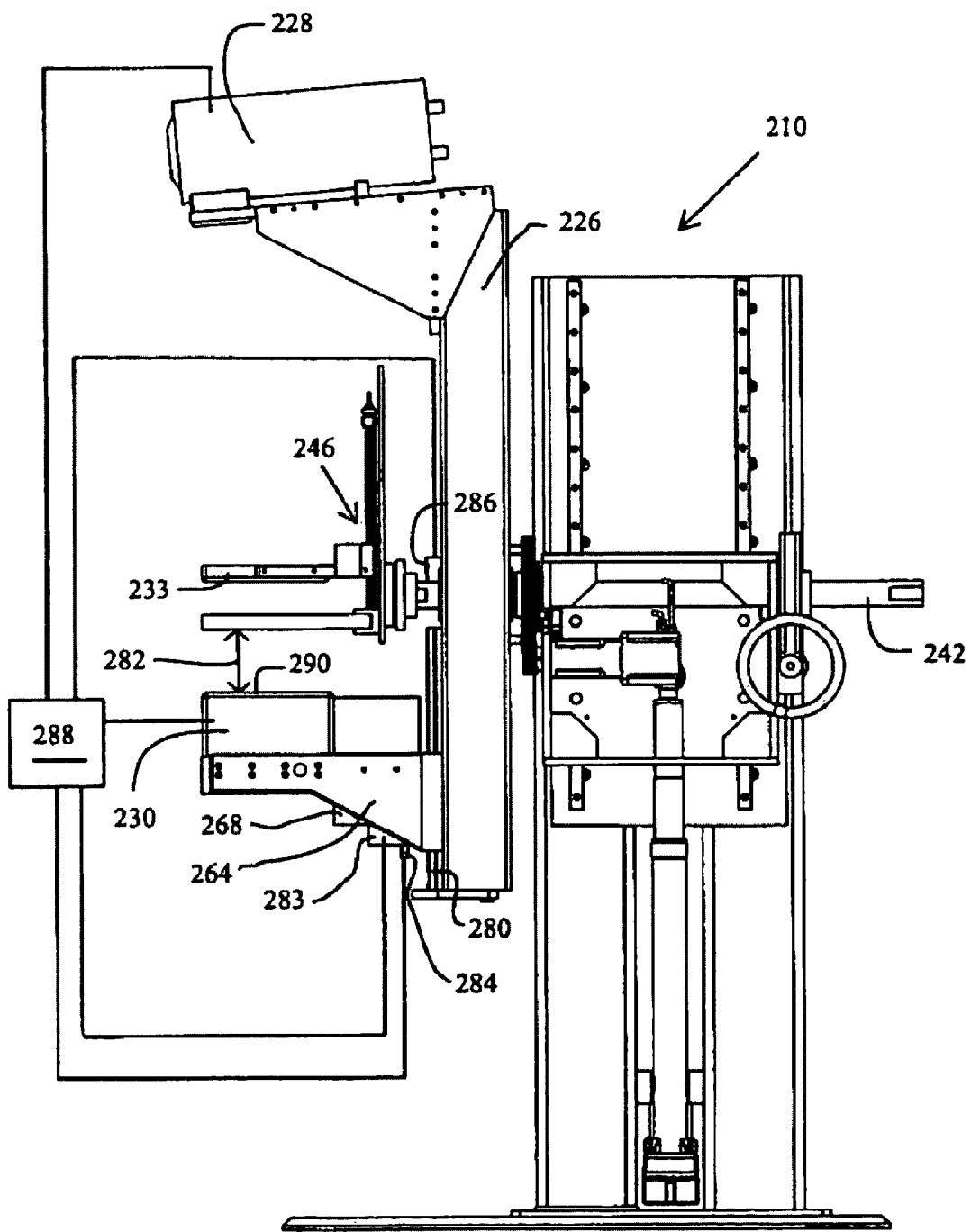
FIG. 7 is a right side elevation view of an alternate embodiment of the imaging apparatus of FIG. 6.

FIG. 7 is a second embodiment of an imaging apparatus in accordance with the present invention. The same reference numbers are used in FIG. 7 as are used in FIGS. 10-12 for the same elements. In this embodiment the mounting bracket 264 of the radiation detector 230 rides on a rail 280 attached to the rotor arm 226. The radiation detector 230 can move on the rail 280 between a first position relatively near the radiation source and a second position relatively far away from the radiation source, as indicated by arrow 282. The radiation detector 230 is illustrated in the second position in FIG. 7. Movement between the first and second positions is driven by a motorized screw drive 283 operatively linked to the mounting bracket 264. Pre-loaded bearings are used between the rail 280 and runner provided on the attachment bracket 264 to minimize movement of the detector relative to the gantry.

In the embodiment illustrated in FIG. 7, the object immobilizer 246 including the platform 232 may be selectively removed from the shaft 242. An indicator switch 286 may be used to assure that the breast support is removed before the detector is moved to its first position. Only when the object immobilizer 246 is removed can the radiation detector 230 be moved into the first position. An encoder 284 is operatively associated with the motorized screw drive 283 allows precise control of the motor position. The object immobilizer 246 may be attached using a quick-release mounting device and mounting pins to insure precise positioning of the support while enabling ready detachment. Limit/indicator switches (not shown) can be used to determine if the detector is at the top or the bottom. These limit switches also provide "homing" positions for validation of the encoded position.

As illustrated schematically in FIG. 7, a controller 288 may be linked to the radiation source 228, the radiation detector 230, the motorized screw drive 232, the encoder 284 and the switch 286. In this embodiment the controller can prevent movement of the radiation source 228 from its second position to its first position without removal of the object immobilizer 246. Likewise, the radiation source 228 can be moved from its first to its second position only with the object immobilizer 246 installed.

The second embodiment discussed with respect to FIG. 7 allows the imaging apparatus 210 to be used either for standard mammography (2-D mammography) or tomosynthesis (3-D mammography). In standard mammography, the breast is generally positioned directly against the detector surface 290. Optionally, an anti-scatter grid may also be inserted between the detector surface 290 and the breast. For use in standard mammography, the source and detector have their vertical orientation illustrated in FIG. 7. The object immobilizer 246 is removed and the radiation source 228 is moved to its first position. In using the imaging apparatus 210 in tomosynthesis implementations, it is desirable to move the detector relative to the breast as described above. In this case the breast immobilizer 246 must be used to immobilize the breast and the radiation detector must be moved to its second position.

The gantry would normally be balanced around its rotational axis only with the radiation detector in its second position. As a result, rapid rotation of the gantry for collection of tomosynthesis images would only be allowed with the radiation detector in the second position. Because movement of the detector into the first position results in an unbalance gantry, the controller 288 allows only low-speed rotations or no rotation in this configuration. To overcome this problem, the weights 268 may be attached to a motor drive which moves the weights in an direction opposite the radiation detector to maintain balance of the radiation detector and the source about the axis of rotation at all times.

The embodiment illustrated in FIG. 7 contemplates the breast immobilizer 246 as being removable. In yet another alternative embodiment the platform 232 may be sufficiently thin to allow the detector to be raised to first position without removal of the breast immobilizer 246. In any embodiment, a suitable anti-scatter grid may be placed between the breast and the radiation detector.

EXAMPLES

The following examples are provided for illustrative purposes only and are not intended to limit the scope of the invention.

Example 1

Breast Imaging with Variable Angular Position.

The object of Example 1 is to simulate the data necessary to generate a three dimensional representation of a breast with resolution of 0.05 mm×0.05 mm×1.0 mm using 13 images collected at non-uniform spacing. In particular, the images are to be taken from −90° to +90° at the angles illustrated in FIG. 8 and listed the Table 1 below.

TABLE 1

|  | Position | Minimum Resolution | Maximum Linear Velocity |
|---|---|---|---|
| Vertical Resolution | 1.00 | −90 | 1.000 | 39.0 |
| Horizontal Resolution | 0.05 | −45 | 0.708 | 27.6 |
| Exposure Time | 0.026 | −30 | 0.502 | 19.6 |
| Detector Distance | 150 | −20 | 0.345 | 13.5 |
| Acceleration | 200 | −12 | 0.214 | 8.3 |
| Maximum Velocity | 200 | −5 | 0.100 | 3.9 |
|  |  | 0 | 0.050 | 2.0 |
|  |  | 5 | 0.100 | 3.9 |
|  |  | 12 | 0.214 | 8.3 |
|  |  | 20 | 0.345 | 13.5 |
|  |  | 30 | 0.502 | 19.6 |
|  |  | 45 | 0.708 | 27.6 |
|  |  | 90 | 1.000 | 39.0 |

Figure 8:
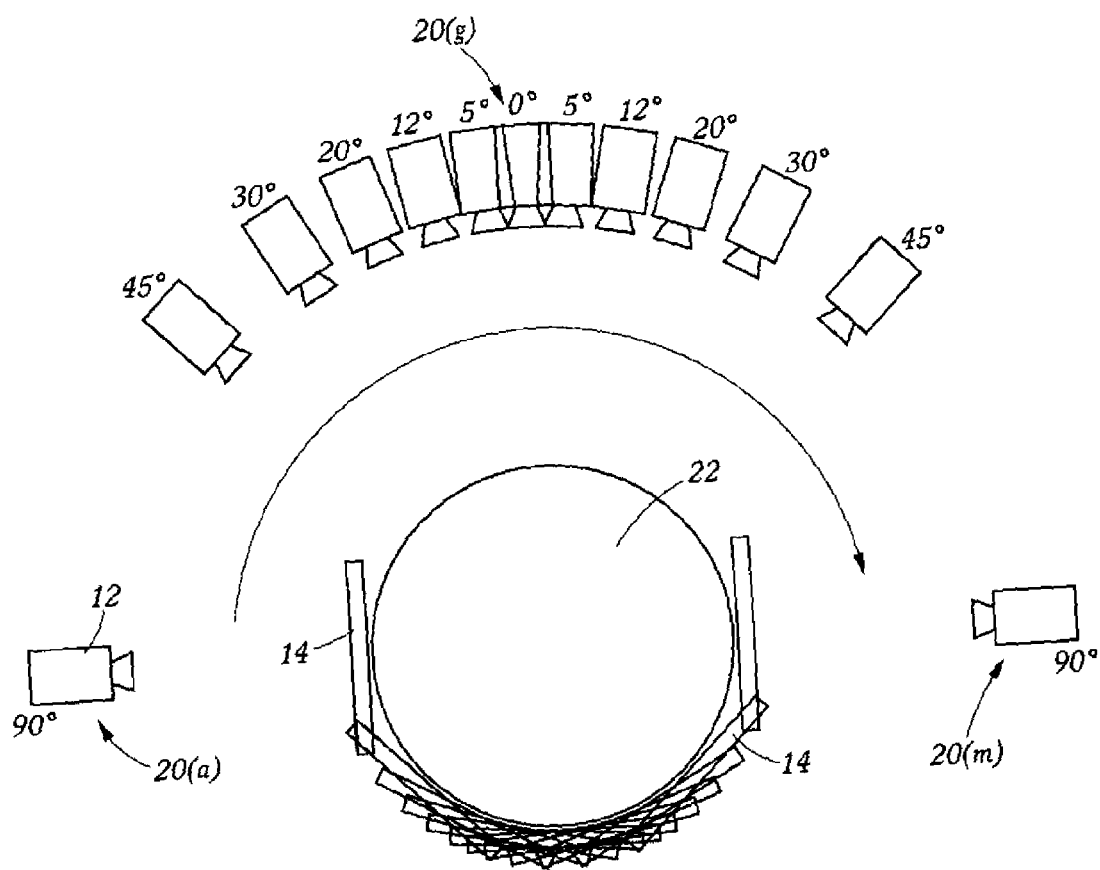
FIG. 8 is a schematic representation of a source detector movement for capturing images described in the examples.
Figure 9:
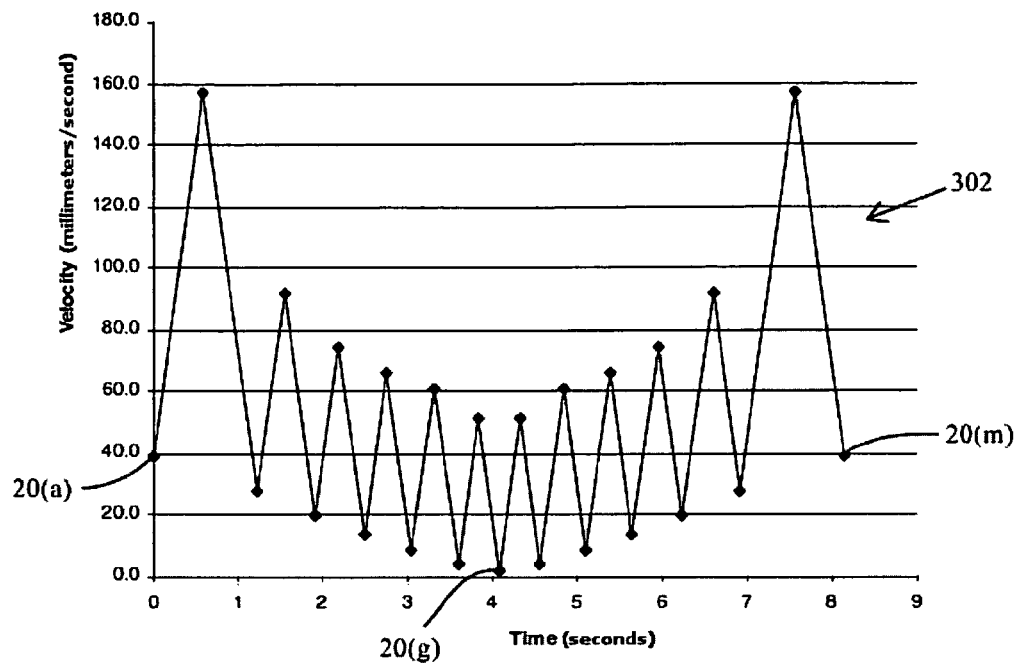
FIG. 9 is a graphical representation of velocity versus time for Example 1.

The data represented in Example 1 is graphically illustrated in FIG. 9. In this example, the imaging procedure utilizes a typical mammography x-ray source operated at 35 keV for a total output dosage of 80 mAs (milliamp seconds). If the source is capable of generating a current of 240 mA, and if the images are each acquired for an equal time, then each image will have an acquisition time (t) of approximately 0.026 seconds assuming an equal radiation dosage at each imaging position 20 2(a-m) (FIG. 8). The resolution required at each position can be approximately calculated by the following formula:

$$r = \sqrt{r_1^2 \sin^2(\theta) + r_2^2 \cos^2(\theta)}$$  Equation (1)

Where r1 is the desired vertical resolution and r2 is the desired horizontal resolution. The linear velocity of the detector 14 at each imaging position 20 is then the resolution (r) times the acquisition time (t). In this example, the resolution at the first imaging position 20a (−90°) is 1 mm, which results in a linear velocity of 39 mm/second. Similarly, the velocity at imaging position 20g (0°), the highest resolution imaging position, is only 2.0 mm/second. In an alternate embodiment, it may be desirable to completely stop the source 12 at the highest resolution position. In either embodiment the velocity at any imaging position may be selected to achieve a desired resolution. Furthermore, the velocity may actually be varied through the imaging position with an average velocity selected to achieve a target resolution.

In between each of the imaging positions, the detector and source are accelerated and/or decelerated (as appropriate) by an acceleration (a). In this example, the acceleration rate is 200 mm/sec2. The complete simulated velocity profile 302 is shown in FIG. 9.

This method results in two substantial improvements relative to methods that cause the detector and source to come to a complete stop for each acquired image. First, the total image acquisition is minimized; and second, mechanical instabilities potentially introduced when the source and detector are stopped are eliminated. Either of these advantages alone would warrant the use of this method.

Example 2

Breast Imaging with Variable Angular Positions and Variable Radiation Dose.

Example 2 is a representation of the data necessary to generate a three dimensional representation of a breast with resolution of 0.05 mm×0.05×1.0 also using 13 images collected at non-uniform spacing. Thus, the apparatus set up and image acquisition technique for Example 2 are the same as described above with respect to Example 1. In Example 2, however, the radiation dose for the various imaging positions 20a-m (FIG. 8) is not assumed to be constant.

Any variable dosing scheme may be implemented with the techniques described herein to achieve desired imaging goals. In Example 2 the relative radiation dose applied at the lower resolution position (20a and 20m) is less than the relative radiation dose applied at the highest resolution position (20g). The relative radiation dosages for each position are included in Table 2 below. It is important to note that the variable radiation dosage plan illustrated in Table 2 is merely illustrative of one possible radiation dosage plan.

TABLE 2

|  | Relative Dose | Position | Minimum Resolution | Maximum Linear Velocity |
|---|---|---|---|---|
| Vertical Resolution | 1.00 | 40 | −90 | 1.000 | 66.0 |
| Horizontal Resolution | 0.05 | 50 | −45 | 0.708 | 37.4 |
| Exposure Time (Total) | 0.333 | 60 | −30 | 0.502 | 22.1 |
| Detector Distance | 150 | 70 | −20 | 0.345 | 13.0 |
| Acceleration | 200 | 80 | −12 | 0.214 | 7.0 |
| Maximum Velocity | 200 | 90 | −5 | 0.100 | 2.9 |
|  |  | 100 | 0 | 0.050 | 1.3 |
|  |  | 90 | 5 | 0.100 | 2.9 |
|  |  | 80 | 12 | 0.214 | 7.0 |
|  |  | 70 | 20 | 0.345 | 13.0 |
|  |  | 60 | 30 | 0.502 | 22.1 |
|  |  | 50 | 45 | 0.708 | 37.4 |
|  |  | 40 | 90 | 1.000 | 66.0 |

Figure 10:
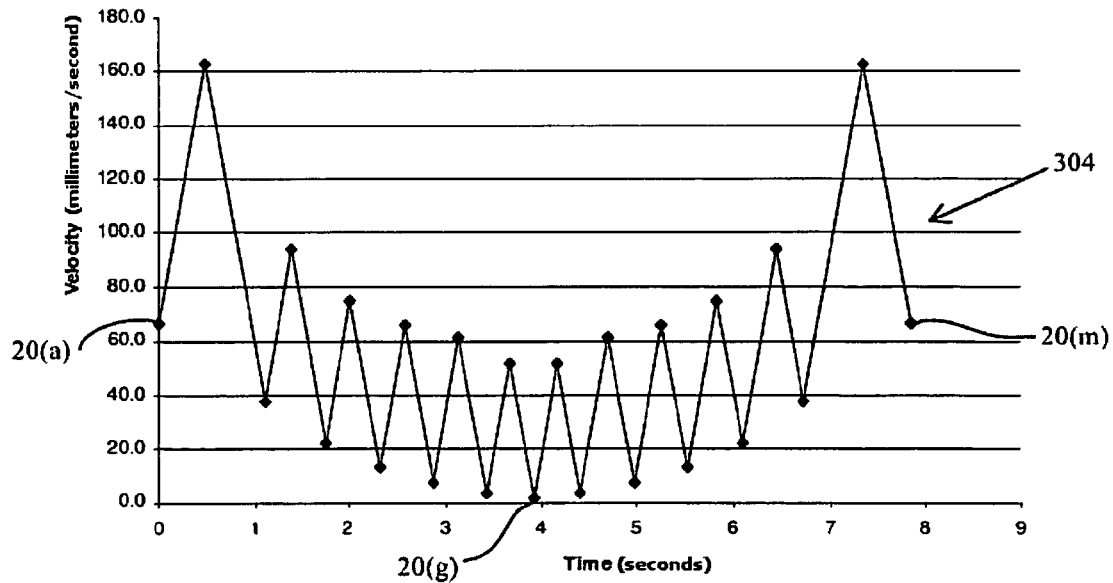
FIG. 10 is a graphical representation of velocity versus time for Example 2.

The data represented by Example 2 is graphically illustrated by velocity profile 304 of FIG. 10. It may be noted by comparing FIG. 10 with FIG. 9 that the overall imaging time is not substantially decreased by the variable radiation dose selected for the Example 2 data representation. The overall radiation dosage received by a patient may be decreased however, without a corresponding time penalty. Other radiation dosage plans may be selected to decrease imaging time as well.

Example 3

Breast Imaging with Variable Angular Position, without Acceleration Between Imagine Positions.

Example 3 is a representation of the data necessary to generate a three dimensional representation of a breast with resolution of 0.05 mm×0.05×1.0 mm using 13 images collected at non-uniform spacing as described above with respect to Examples 1 and 2. In the Example 3 simulation, however, there is no acceleration and deceleration in between each imaging position 20(a-m). The data simulated in Example 3 thus varies from that of Examples 1 and 2 in that the source is smoothly decelerated from a maximum linear velocity of 39.0 mm/second at imaging position 20a through a minimum linear velocity of 2.0 mm/second at imagine position 20g. The source 12 is then smoothly accelerated to the maximum linear velocity of 39.0 mm/second at position 20m. Other acceleration profiles which might include full stoppage at one or more select imaging positions are within the scope of the invention. A simulated velocity profile 306 is shown graphically in FIG. 11.

Figure 11:
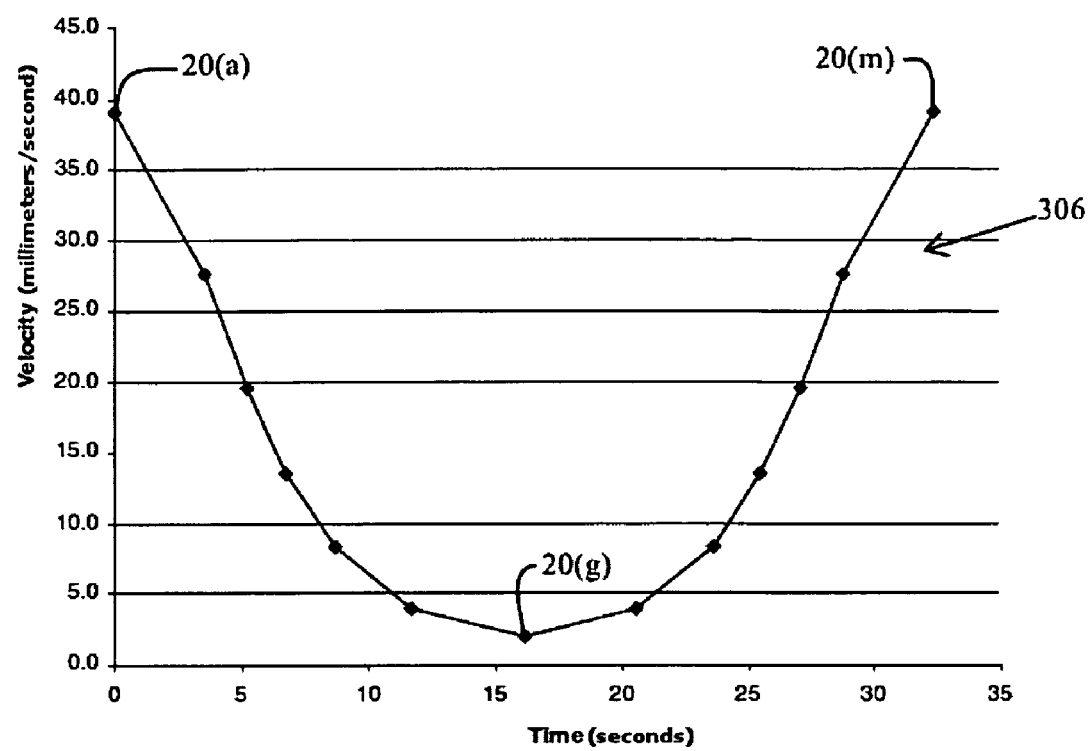
FIG. 11 is a graphical representation of velocity versus time for Example 3.

It may be noted by a comparison of Example 3 with Example 1 that the overall imaging time is increased from approximately 8 seconds to approximately 32 seconds when acceleration and deceleration between each imaging position 20a-m is not utilized. Mechanical and control system complexity is however avoided by using a smooth velocity profile such as is illustrated in Example 3. In addition, mechanical instabilities potentially introduced during various acceleration/deceleration phases may be minimized by implementing a smooth velocity profile. The total image acquisition time simulated in Example 3 and illustrated in FIG. 11 is still substantially less than the image acquisition time of 235 seconds which would be experienced if the minimum velocity of 2.0 mm/second were employed for all imaging positions 20a-m.

Example 4

Breast Imaging Using Closely Spaced, Equal Angle Projections.

The object of Example 4 is to simulate the data necessary to generate an image of a breast with resolution of 0.05 mm×0.05 mm×1.0 mm using 61 images collected at uniform spacing. In particular, the images are to be taken from −30° to +30° with an angular separation of 1° between image positions. For illustration, it is assumed that the imaging procedure will utilize a typical mammography x-ray source operated at 35 keV for a total dosage of 80 mAs (milliamp seconds). If the source is capable of generating a current of 240 mA, and if the images are each acquired for an equal time, each image will have an acquisition time of approximately 0.006 seconds. The resolution required at each position can be approximately calculated from Equation 1.

As in the previous examples, the linear velocity of the detector at a select imaging position is then the resolution (r) times the acquisition time (t). In this example, the resolution at the first imaging position 20a' (−30°) is 0.5 mm, which results in a linear velocity of 90.3 mm/second. Similarly, the velocity at imaging position 20b' 0° (which requires higher resolution of 0.05 m) is 9.0 mm/second. Thus the utilized imaging velocity may be selected to achieve or preserve a target resolution.

Figure 12A:
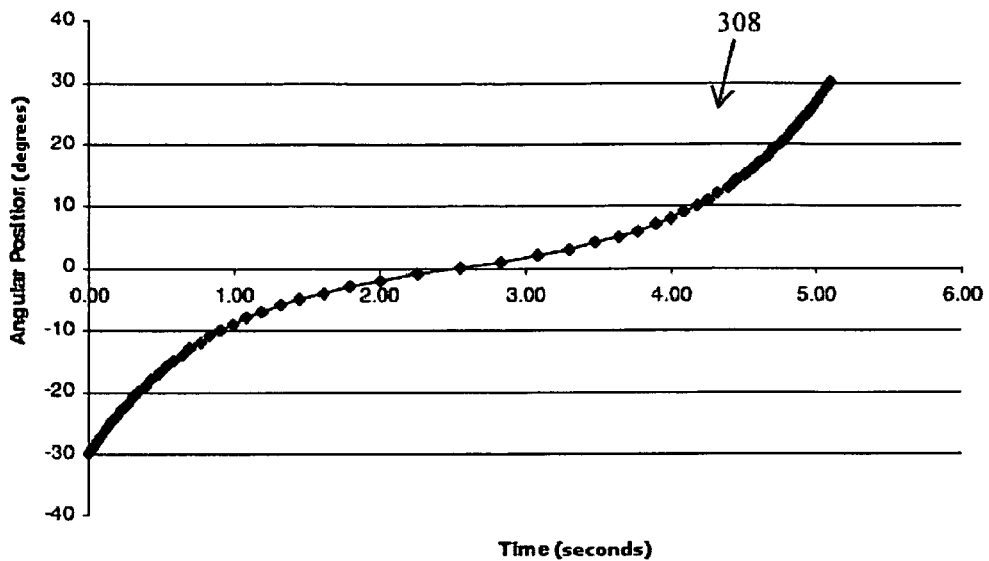
FIGS. 12A and 12B are graphical representations of angular position versus time for Example 4.

In between each of the imaging positions, the detector and source are accelerated and decelerated (as appropriate) to the velocity desired for the next imaging position. A complete trajectory profile 308 (position vs. time) is shown in FIG. 12A. Note that in FIG. 12A, the increasing slope of the curve at the higher angles reflects the higher velocity at higher angles.

Figure 12B:
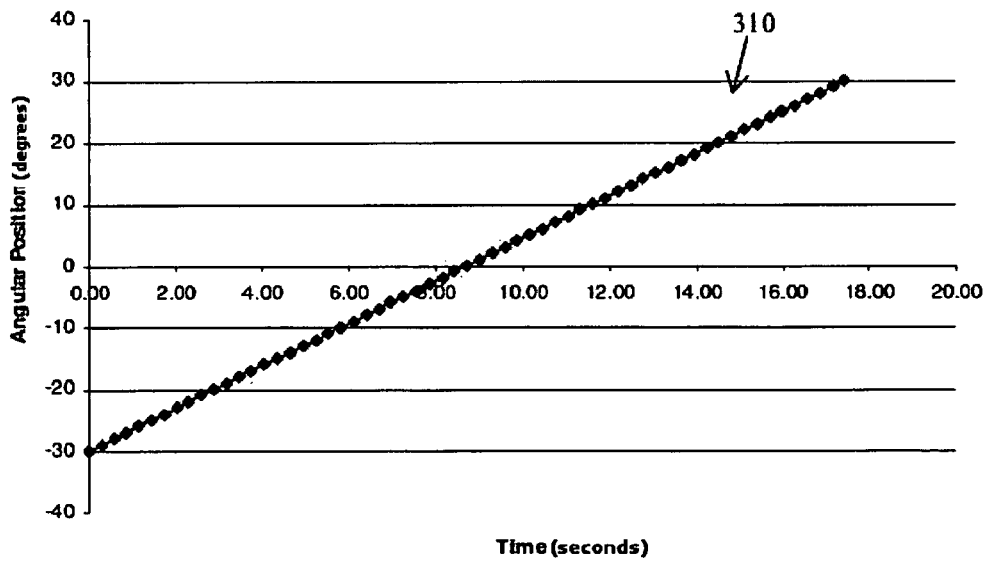

For comparison, a trajectory profile 310 is also calculated for the case illustrated in FIG. 12B where the velocity is held fixed to the maximum speed appropriate for the highest resolution. Thus, in the Example illustrated in FIG. 12B velocity is held constant at the 9.0 mm/second rate appropriate for 0.05 mm resolution. Note that the total imaging time increases from approximately 5 seconds to over 17 seconds.

The decrease in the acquisition time provided by the variable velocity method is a very significant factor, particularly in implementations where motion may occur during the image acquisition. For example, in breast imaging, it is generally believed that the acquisition time should be kept to a minimum, preferably below 10 seconds.

The methods disclosed herein may be used with a multi-resolution detector. For example, at each angular position, the detector can be operated at a resolution approximating the imaging resolution required at that position. For example, in Example 1 above, the necessary resolution at −90° is 1 mm while at 0° it is 0.05 mm. A multi-resolution detector can be operated at the corresponding resolution at each position. Depending on the specific properties of the detector, this could result in a) a decreased readout time for at the low-resolution positions and/or b) decreased noise at the low-resolution positions.

The variable velocity method may be used with or without varying dose as a function of angle. For example, at each angular position, the appropriate dose can be calculated that provides adequate statistical precision for the resolution required at that position. For example, in Example 1 above, a lower dose could be used at +/−90° than is used at 0°. This could result in a) decreased exposure times and/or b) decrease dose provide to the object. In particular, it may be noted that decreasing the dose at the lower-resolution position could reduce the exposure time, leading to a corresponding increase in the allowed velocity at that position. Further considering Example 1, if the dose is halved at the +/−90° positions, then the velocity at each of these position can be doubled to 78 mm/sec.

While a number of embodiments are particularly shown and described herein, it would be understood by those skilled in the art that changes in the form and details may be made to the various embodiments disclosed herein without departing from the spirit and scope of the invention and that the various embodiments disclosed herein are not intended to act as limitations on the scope of the claims.

What is claimed is:

1. A method of imaging an object comprising:
projecting radiation from a radiation source through an object;
moving the radiation source through multiple imaging positions relative to the object while projecting radiation at more than one of the imaging positions;
causing the radiation source to move at a selected first source velocity for at least one imaging position which first source velocity is different from another selected source velocity for a second imaging position, wherein the multiple imaging positions have non-uniform angular spacing with respect to the object, and wherein the radiation source is caused to move at the first or second source velocity to achieve a resolution desired for data collected at the select imaging position; wherein the image resolution in a first plane through the object is higher than the image resolution in a second plane through the object, said second plane being orthogonal to said first plane; and
detecting the radiation transmitted through the object.

2. The method of claim 1 further comprising projecting radiation only while moving the radiation source through the multiple imaging positions.

3. The method of imaging an object of claim 1 wherein the velocity of the radiation source is varied within a select imaging position.

4. The method of imaging an object of claim 1 wherein the radiation source is accelerated or decelerated between imaging positions.

5. The method of imaging an object of claim 1 wherein the motion of the radiation source is stopped at one or more of the imaging positions.

6. The method of imaging an object of claim 1 further comprising projecting radiation at a select dosage for one imaging position that is different from the radiation dosage selected for a second imaging position.

7. The method of imaging an object of claim 6 wherein the resolution dosage selected for at least one select imaging position is related to a resolution desired for data collected at the select imaging position.

8. A method of imaging an object comprising:
projecting radiation from a radiation source through an object;
moving the radiation source through multiple imaging positions relative to the object without stopping movement of the source while projecting radiation at more than one of the imaging positions wherein the multiple imaging positions have non-uniform angular spacing with respect to the object;
causing the radiation source to move at a selected first source velocity for at least one imaging position which first source velocity is different from another selected source velocity for a second imaging position, wherein the radiation source is caused to move at the first or second source velocity to achieve a resolution desired for data collected at the select imaging position; wherein the image resolution in a first plane through the object is higher than the image resolution in a second plane through the object, said second plane being orthogonal to said first plane; and
detecting the radiation transmitted through the object.

9. The method of claim 8 further comprising projecting radiation only while moving the radiation source through the multiple imaging positions.

10. An apparatus for imaging an object comprising:
A radiation source for projecting radiation through an object;
means for moving the radiation source through multiple imaging positions relative to the object wherein movement of the source is not stopped while projecting radiation at more than one of the imaging positions wherein the multiple imaging positions have non-uniform angular spacing with respect to the object and the radiation source is caused to move at a selected first source velocity for at least one imaging position which first source velocity is different from another selected source velocity for a second imaging position, wherein the radiation source is caused to move at the first or second source velocity to achieve a resolution desired for data collected at the select imaging position; wherein the image resolution in a first plane through the object is higher than the image resolution in a second plane through the object, said second plane being orthogonal to said first plane; and
means for detecting the radiation transmitted through the object.

11. The apparatus of claim 10 wherein the projecting means projects radiation through the object only when moving through an imaging position.

12. The apparatus for imaging an object of claim 10 wherein the radiation source is accelerated or decelerated between imaging positions.

13. The apparatus for imaging an object of claim 10 wherein the motion of the imaging source is not stopped while moving through each of the multiple imaging positions.

14. The apparatus for claim 10 further comprising means for projecting radiation at a select dosage for one imaging position that is different from the radiation dosage selected for a second imaging position.

15. An imaging apparatus comprising:
a radiation source;
a radiation detector having a detection surface;
the radiation source and the radiation detector being coupled for rotation in an X-Z plane about an axis of rotation while maintaining radiation communication therebetween, the radiation detector further being configured for movement between a first position relatively near the radiation source and a second position relatively far from the radiation source;
means for accelerating and decelerating the radiation source and detector between multiple imaging positions which have non-uniform angular spacing with respect to the object;
a removable platform configured in operative engagement with the radiation source and radiation detector to maintain an object in a fixed position between the radiation source and the radiation detector;
the radiation source, the radiation detector and the removable platform being configured so that with the radiation source and the radiation detector aligned along the Z-axis and the platform removed, the radiation detector is movable into the first position; and
the radiation source, the radiation detector and the removable platform being configured so that the radiation detector is movable into the second position only with the platform in operative association with the radiation source and the radiation detector.

16. An imaging apparatus comprising:
a radiation source;
a radiation detector;
rotating means for rotating the radiation source and radiation detector in an X-Z plane about an axis of rotation while maintaining radiation communication therebetween;
means for securing an object between the radiation source and detector;
means for accelerating and decelerating the radiation source and detector between multiple imaging positions which have non-uniform angular spacing with respect to the object;
damping means for damping vibration of the radiation source, radiation detector and the securing means relative to one another during rotating of the radiation source and radiation detector; and
the damping means providing a sufficiently high harmonic frequency to substantially settle the radiation source, the radiation detector and the platform within about 0.067 seconds.

* * * * *